US008580793B2

United States Patent
Scaburri et al.

(10) Patent No.: US 8,580,793 B2
(45) Date of Patent: Nov. 12, 2013

(54) USE OF KINASE INHIBITOR FOR THE TREATMENT OF THYMOMA

(75) Inventors: Angela Scaburri, Legnano (IT); Maria Adele Pacciarini, Milan (IT); Marina Ciomei, Corsico (IT); Bernard Laffranchi, Bubbiano (IT); Silvia Comis, Bubbiano (IT)

(73) Assignee: Nerviano Medical Services S.r.l., Nerviano (MI) (IT)

( * ) Notice: Subject to any disclaimer, the term of this patent is extended or adjusted under 35 U.S.C. 154(b) by 0 days.

(21) Appl. No.: 13/256,467

(22) PCT Filed: Mar. 15, 2010

(86) PCT No.: PCT/EP2010/053311
§ 371 (c)(1),
(2), (4) Date: Dec. 6, 2011

(87) PCT Pub. No.: WO2010/106028
PCT Pub. Date: Sep. 23, 2010

(65) Prior Publication Data
US 2012/0077819 A1  Mar. 29, 2012

(30) Foreign Application Priority Data
Mar. 20, 2009  (EP) ..................................... 09155745

(51) Int. Cl.
*A61K 31/497*  (2006.01)
*C07D 491/00*  (2006.01)

(52) U.S. Cl.
USPC ...................................... 514/252.16; 544/251

(58) Field of Classification Search
USPC ...................................... 514/252.16; 544/251
See application file for complete search history.

(56) References Cited

FOREIGN PATENT DOCUMENTS

| WO | WO 2004/104007 A1 | | 12/2004 |
|---|---|---|---|
| WO | WO 2004104007 A1 | * | 12/2004 |
| WO | WO 2007/090794 A1 | | 8/2007 |
| WO | WO 2008/025512 A1 | | 3/2008 |

OTHER PUBLICATIONS

Brasca, M.G., et al. "Identification of N,1,4,4-Tetramethyl-8-{[4-(4-methylpiperazin-1-yl)phenyl]amino}-4,5-dihydro-1H-pyrazolo[4,3-h]quinazoline-3-carboxamide (PHA-848125), a Potent, Orally Available Cyclin Dependent Kinase Inhibitor." J. Med. Chem. (2009), vol. 52, pp. 5152-5163.*
Kim, D.J., et al. "Expression of neurotrophin receptors in surgically resected thymic epithelial tumors." European Journal of Cardio-Thoracic Surgery. (2005), vol. 28, pp. 611-616.*
Yokoi, K. "Multidisciplinary Treatment for Advanced Invasive Thymoma with Cisplatin, Doxorubicin, and Methylprednisolone." Journal of Thoracic Oncology. (Jan. 2007), vol. 2, No. 1, pp. 78.*
Wright, C.D. "Management of thymomas." Critical Reviews in Oncology/Hematology. (2008), vol. 65, pp. 109-120.*
Engels E.A. et al., "Malignant Thymoma in the United States: Demographic Patterns in Incidence and Associations with Subsequent Malignancies", *Int. J. Cancer* 105:546-551 (2003).
Wright C.D., "Management of Thymomas", *Critical Reviews in Oncology/Hematology* 65:109-120 (2008).
Kim D-J et al., "Expression of Neurotrophin Receptors in Surgically Resected Thymic Epithelial Tumors", *European Journal of Cardio-Thoracic Surgery* 28:611-616 (2005).
Kondo K., "Optimal Therapy for Thymoma", *The Journal of Medical Investigation* 55:17-28 (2008).
Yokoi K. et al., "Multidisciplinary Treatment for Advanced Invasive Thymoma With Cisplatin, Doxorubicin, and Methylprednisolone", *Journal of Thoracic Oncology* 2(1):73-78 (Jan. 2007).
Therasse P. et al., "New Guidelines to Evaluate the Response to Treatment in Solid Tumors", *Journal of the National Cancer Institute* 92(3):205-216 (Feb. 2, 2000).
International Search Report dated May 21, 2010 received from the European Patent Office in related International Application No. PCT/EP2010/053311.

* cited by examiner

*Primary Examiner* — Andrew D Kosar
*Assistant Examiner* — John S Kenyon
(74) *Attorney, Agent, or Firm* — Scully, Scott, Murphy & Presser, P.C.

(57) ABSTRACT

The invention provides a low molecular weight ATP-competitive CDK inhibitor and TRKA inhibitor of formula (I) for use in the treatment of thymoma and thymic carcinoma. The compound can be administered together with one or more cytotoxic or cytostatic agents.

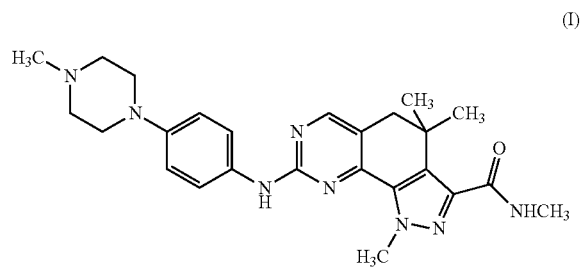

(I)

4 Claims, No Drawings

USE OF KINASE INHIBITOR FOR THE TREATMENT OF THYMOMA

TECHNICAL FIELD

The present invention relates to the treatment of thymoma and thymic carcinoma patients through the use of a low molecular weight ATP-competitive CDK (Cyclin-Dependent Kinase) and Tropomyosin-Related Kinase A (TRKA) inhibitor.

BACKGROUND ART

Thymoma is a rare tumor, but nevertheless is the most common neoplasm of the anterior mediastinal compartment. The overall incidence of malignant thymoma in US (1973-1998) was 0.15 per 100000 person/years (849 cases) [Source: "Malignant thymoma in the United States: demographic patterns in incidence and associations with subsequent malignancies" Int. J. Cancer, 2003; 105(4): 546-51]. Thymoma is considered to have an indolent growth, but it has a potential for local invasion, pleural dissemination and distant metastases. Patients with locally advanced or disseminated thymoma are usually symptomatic, presenting with chest pain, shortness of breath, paralysis of the phrenic nerve, pleural effusion and superior vena cava syndrome. Immune disorders have also been associated with thymoma, the most common being myasthenia gravis (Wright C. Management of thymomas. Crit. Rev. Oncol. Hematol., 2008; 65(2): 109-20). Thymic carcinomas are usually advanced at diagnosis, have a higher recurrence rate and a worse prognosis (survival) compared with other thymomas (NCI PDQ [Physician Data Query]®, last modified May 8, 2008).

TRKA seems to play a significant role in the biology of thymoma. Expression of neurotrophin receptors was indeed specifically documented in thymic epithelial tumors on a quite large series of patients (99 patients) (Kim D J, Yang W I, Kim S H, Park I K, Chung K Y. Expression of neurotrophin receptors in surgically resected thymic epithelial tumors. Eur. J. Cardiothorac. Surg., 2005; 28(4): 611-6). In this study, the pattern of TRKA expression was analyzed according to WHO classification for the histologic subtypes of thymic tumors. All tumor types (namely A, AB, B1, B2, B3, C) were found to evidence (by immunostaining) the presence of TRKA and the proportion of tumors which demonstrated intense immunoreactivity gradually increased from type A to type C. Conversely, any type of thymoma showed TRKB or TRKC immunoreactivity, thus suggesting a specific role (to be anyway further elucidated) for TRKA in this disease.

Besides the above mentioned WHO histological classification of thymoma, the Masaoka staging system is commonly employed to evaluate invasiveness and to base the therapeutic choice, since the optimal treatment for this disease depends on its clinical stage (NCI PDQ [Physician Data Query] ®, last modified May 8, 2008). Surgery (with or without radiotherapy) is the mainstay of early-stage thymoma treatment, because in most cases the disease is localized. Radiation and chemotherapy are generally widely applied as adjuvant and palliative procedures. (Kondo K. Optimal therapy for thymoma. J. Med. Invest., 2008; 55(1-2): 17-28). Advanced invasive thymomas (such as tumors with great vessel invasion, pleural and/or pericardial dissemination, lymphnode involvement or distant metastases) are not usually manageable by surgical resection or radiotherapy alone (Yokoi K, Matsuguma H, Nakahara R, Kondo T, Kamiyama Y, Mori K, et al. Multidisciplinary treatment for advanced invasive thymoma with cisplatin, doxorubicin, and methylprednisolone. J. Thorac. Oncol. 2007; 2(1): 73-8). Locally advanced or metastatic thymomas are often treated with combined treatment modalities, including radiation and chemotherapy. Thymomas are generally chemosensitive tumors. Chemotherapy was shown indeed to have significant antitumor activity against unresectable, recurrent or metastatic thymomas, producing an overall objective response in an average of two thirds of patients and complete remissions in one third. Cisplatin/doxorubicin-based combination chemotherapy [PAC regimen (cisplatin, doxorubicin, cyclophosphamide) or ADOC regimen (doxorubicin, cisplatin, vincristine, cyclophosphamide)] seem to produce the best overall response rate and survival. Other combined and/or single agent chemotherapy with cisplatin, etoposide, ifosfamide, epirubicin, maytansine and steroids are used as well (Kondo K., 2008, see above). Optimal treatment strategy has anyway not yet been determined and other drugs are warranted to improve the outcome of patients with advanced invasive tumors (Yokoi K, 2007).

There is therefore an unmet medical need for new potent agents for the treatment of thymoma and in particular of thymic carcinoma. The present invention addresses this problem.

SUMMARY OF THE INVENTION

The invention provides a low molecular weight compound capable of inhibiting CDKs (in particular CDK2/Cyclin A complex) and TRKA signalling pathways and efficacious in inhibiting the proliferation of thymoma and in particular of thymic carcinoma.

The compound of the present invention showing the desired activity is a pyrazoloquinazoline designed to target the ATP pocket of protein kinases. The compound has revealed to be a potent ATP-competitive inhibitor of CDKs. The compound has been found to display a significant inhibitory potency also towards TRKA.

In view of its biological activity, the compound of the invention offers a new path for the development of a treatment for the patient population suffering from thymoma and thymic carcinoma.

Indeed in a Phase I study two thymic carcinoma patients reported an objective tumor response.

DETAILED DESCRIPTION OF THE INVENTION

In a first aspect, the present invention relates to a compound of formula (I)

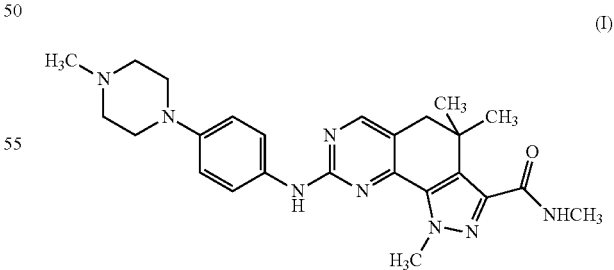

or a pharmaceutically acceptable salt thereof for use in a method for treating a thymoma.

As used herein the term "thymoma" includes the 6 histological categories (types A, AB, B1, B2, B3, C) indicated by the 1999 WHO classification (Rosai J, Sobin L. Histological typing of tumors of the thymus. World Health Organization.

International histological classification of tumours. Heidelberg: Springer-Verlag, 1999) and therefore includes the "thymoma" and "thymic carcinoma" histologies, according to the latest WHO classification (2004) in which thymoma subtype B3 is classified also as differentiated thymic carcinoma and thymoma subtype C is classified as thymic carcinoma (Travis W et al., eds. Pathology and genetics of tumours of the lung, pleura, thymus and heart. World Health Organization classification of tumours. Lyon: IARC Press, 2004).

In a preferred embodiment, the compound of formula (I) above is used in a method for treating a thymic carcinoma.

The compound of formula (I) has the chemical name 8-[4-(4-methyl-piperazin-1-yl)-phenylamino]-1,4,4-trimethyl-4,5-dihydro-1H-pyrazolo[4,3-h]quinazoline-3-carboxylic acid methylamide. It can be prepared as described in WO2004104007, is endowed with protein kinase inhibitory activity and is thus useful in therapy as antitumor agent. In particular, the preferred preparation of the compound of formula (I) is that described in example 58 of the above mentioned International Patent Application.

Pharmaceutically acceptable salts of the compound of formula (I) include the acid addition salts with inorganic or organic acids, e.g., nitric, hydrochloric, hydrobromic, sulphuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid and the like.

Within the scope of the claimed invention is the use of all the possible isomers and their admixtures and of both the metabolites and the pharmaceutically acceptable bio-precursors (otherwise referred to as pro-drugs) of the compounds of formula (I). Prodrugs are any covalently bonded compounds, which release the active parent drug, according to formula (I), in vivo.

A therapeutically effective amount of the compound according to formula (I) may be administered to a subject upon determination of the subject as having a disease or unwanted condition that would benefit by treatment with said compound. Medical or clinical personnel may make the determination as part of a diagnosis of a disease or condition in a subject. The compound may also be used in the prevention of such conditions, which may be viewed as reducing the probability of a subject having one or more of the conditions.

As used herein, a "therapeutically effective amount" of a compound refers to an amount sufficient to achieve its intended purpose. Determination of the effective amounts is well within the capability of those skilled in the art based upon the achievement of a desired effect. An effective amount will depend on factors including, but not limited to, the size of a subject and/or the degree to which the disease or unwanted condition from which a subject suffers has progressed. The effective amount will also depend on whether the compound is administered to the subject in a single dosage or periodically over time.

The compound of formula (I) of the present invention is intended for the treatment of subjects. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs and cats; laboratory animals including rodents, such as rats, mice and guinea pigs, and the like. Examples of non-mammals include, but are not limited to, birds, fish and the like.

The term "treating" as used herein includes achieving a therapeutic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder.

Another object of the present invention is a therapeutic combination comprising (a) the compound of formula (I) as defined above and (b) one or more cytotoxic or cytostatic chemical agents, for use in a method for treating a thymoma. Preferably the thymoma is a thymic carcinoma.

Exemplary cytostatic or cytotoxic chemical agents includes alkylating agents (for example Nitrogen Mustards, such as Cyclophosphamide and Ifosfamide), alkylating-like agents (i.e. Platinum derivatives, such as Cisplatin and Carboplatin), topoisomerase II inhibitors [for example Anthracyclines (such as doxorubicin and epirubicin) and Podophillotoxins (such as etoposide)], antimicrotubules agents (such as taxanes, vincristine and maytansine), steroids, hormonal agents, immunological agents, interferon-type agents, cyclooxygenase inhibitors (e.g. COX-2 inhibitors), matrix-metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, and the like.

The present invention also relates to a pharmaceutical composition comprising a compound of formula (I) as defined above admixed with a pharmaceutically acceptable carrier, diluent or excipient, for use in the treatment of thymomas, preferably of thymic carcinomas.

In a further embodiment the pharmaceutical composition according to the invention further comprises one or more cytotoxic or cytostatic chemical agents.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine, methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions or suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

In therapeutic use, the compound of formula (I) is administered to a subject at dosage levels of from about 10 mg/m² to about 400 mg/m² of body surface per day. A dosage level of from about 20 mg/m² to 200 mg/m² constitutes a particularly suitable range. For an adult human subject, a dosage of from about 20 mg to about 800 mg per dose, more preferably from about 40 mg to about 400 mg per dose, from 1 to 28 consecutive days, may be used as a non-limiting example. A preferred schedule of treatment consists of a dose of 150 mg/day for four days of treatment followed by three days of rest for three weeks in a four-week cycle. Alternatively, the following schedules of treatment are also suitable: a dose of 150 mg/day for seven days of treatment followed by seven days of rest in a two-week cycle; or a dose of 48-72 mg/m²/day (corresponding to about 80-120 mg/day) for fourteen days of treatment followed by seven days of rest in a three-week cycle. The above schedules of treatment are intended to be periodically repeated until medically indicated.

Lower or higher doses than those disclosed herein may be used, as required. Such dosages, however, may be altered depending on a number of variables, not limited to the activity of the compound used, the condition to be treated, the mode of administration, the regimen of treatment, the requirements of the individual subject, the severity of the condition being treated and the judgment of the practitioner. The foregoing ranges are merely suggestive, as the number of variables in regard to an individual treatment regime is large and considerable excursions from these recommended values are not uncommon.

With the aim to better illustrate the present invention, without posing any limitation to it, the following examples are now given.

EXAMPLES

Example 1

Scintillation Proximity Assay (SPA) Format for Kinases

This assay allows measurement of the inhibition of the kinase activity of a specific enzyme obtained with test compound. Different kinases can be tested in parallel.

A biotinylated substrate is trans-phosphorylated by a specific kinase in the presence of ATP including a γ33-ATP tracer. At the end of the reaction the phosphorylated substrate is then captured using Streptavidin-coated SPA beads. A dense 5M CsCl solution is added and the mixture is incubated for four hours. This causes the SPA beads to float to the top of the CsCl solution containing the unincorporated radiolabelled ATP.

The extent of phosphorylation is measured using a 13-counter. In these assays, the compound of formula (I) showed a potent inhibitory activity on the CDK2/Cyclin A complex ($IC_{50}$=45 nM), showing activity also towards closely related CDKs, i.e. CDK1, CDK4, and CDK5 ($IC_{50}$=398, 160 and 265 nM, respectively), but also towards Tropomyosin Related Kinase A (TRKA) ($IC_{50}$=53 nM).

Example 2

Objective Tumor Response achieved in a Thymic Carcinoma Patient

An objective tumor response was obtained in a 24 years old female patient, first diagnosed with thymic carcinoma in May 2002 and having had her third progression of disease with metastases to lung in July 2007, entered the phase I clinical trial in September 2007. Treatment with the compound of formula (I) was administered at the daily dose of 150 mg with schedule of treatment encompassing four days of treatment followed by three days of rest for three weeks in a four-week cycle. After 10 cycles of treatment, the patient showed a partial tumor response (PR) as per RECIST criteria in solid tumors (Therasse P, Arbuck S, Eisenhauer E A, Wanders J, Kaplan R S, Rubinstein L, et al. New guidelines to evaluate the response to treatment in solid tumors. J. Natl. Cancer Inst., 2000; 92 (3): 205-216), with a 31.2% decrease in the sum of target lesions compared to baseline; the PR was confirmed one month later and was documented until cycle 13, with a 37.6% decrease in the sum of target lesions compared to baseline. The patient, prior to be treated in the clinical trial, received other treatments for her thymic carcinoma, as follows: from January 2005 to June 2005: Adriamycin®, Cytoxan®, Cisplatin; from February 2006 to May 2006: Ifosfamide; from October 2006 to June 2007: Taxol®, Carboplatin; from June 2007 to July 2007: Adriamycin®, Cytoxan®, Vincristine. The patient had also surgery in May 2002 and radiotherapy in July 2002 and July 2006.

Example 3

Objective Tumor Response Achieved in a Second Thymic Carcinoma Patient

Another objective tumor response was obtained in a 62 years old male patient, first diagnosed with thymic carcinoma in May 2006, becoming metastatic to lung, bones and peritoneum in October 2007. The patient started treatment in the phase I clinical trial in December 2008. Treatment with the compound of formula (I) was administered at the daily dose of 150 mg with schedule of treatment encompassing four days of treatment followed by three days of rest for three weeks in a four-week cycle. After 6 cycles of treatment, the patient showed a partial tumor response (PR) as per RECIST criteria with a 30% decrease in the sum of target lesions compared to baseline and stable non-target lesions; the PR was confirmed one month later, with a 40% decrease in the sum of target lesions compared to baseline and stable non-target lesions. The patient, prior to be treated in the clinical trial, received one line of chemotherapy (cisplatin/gemcitabine) from November 2007 to March 2008; he had surgery in May 2006 and radiotherapy in September 2006.

The invention claimed is:

1. A method of treating thymoma in a patient in need thereof comprising administering to said patient a therapeutically effective amount of a pharmaceutical composition comprising a compound of formula (I)

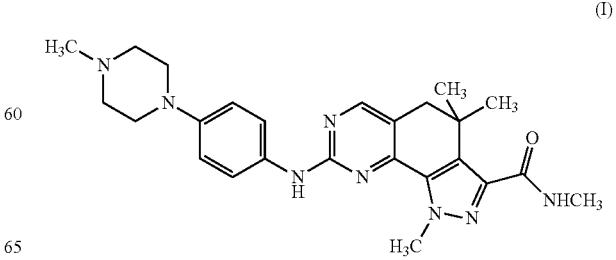

or a pharmaceutically acceptable salt thereof, admixed with a pharmaceutically acceptable carrier, diluent or excipient.

2. The method according to claim 1 wherein the thymoma is a thymic carcinoma.

3. A method of treating thymoma in a patient in need thereof comprising:
administering to said patient a therapeutically effective amount of a pharmaceutical composition comprising a compound of formula (I)

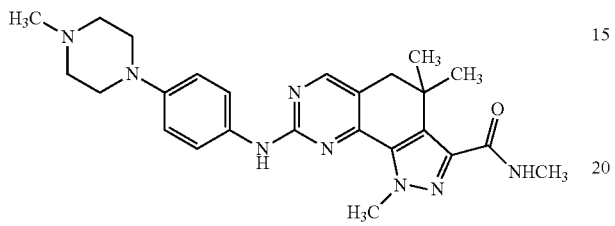

(I)

or a pharmaceutically acceptable salt thereof, admixed with a pharmaceutically acceptable carrier, diluent or excipient and one or more cytotoxic or cytostatic chemical agents.

4. The method according to claim 3 wherein the thymoma is a thymic carcinoma.

* * * * *